US011857559B2

(12) United States Patent
Barik et al.

(10) Patent No.: US 11,857,559 B2
(45) Date of Patent: Jan. 2, 2024

(54) PHARMACEUTICAL COMPOSITION COMPRISING CANAGLIFLOZIN, PROCESS OF PREPARATION AND USE THEREOF

(71) Applicants: Satyabrata Barik, Hyderabad (IN); Venugopala Chokkasandra Jayarama Reddy, Hyderabad (IN); Sivakumaran Meenakshisunderam, Hyderabad (IN)

(72) Inventors: Satyabrata Barik, Hyderabad (IN); Venugopala Chokkasandra Jayarama Reddy, Hyderabad (IN); Sivakumaran Meenakshisunderam, Hyderabad (IN)

(73) Assignee: Aurobindo Pharma Ltd.

( * ) Notice: Subject to any disclaimer, the term of this patent is extended or adjusted under 35 U.S.C. 154(b) by 77 days.

(21) Appl. No.: 17/100,829

(22) Filed: Nov. 21, 2020

(65) Prior Publication Data
US 2021/0085704 A1    Mar. 25, 2021

Related U.S. Application Data (63) Continuation-in-part of application No. 16/083,534, filed on Sep. 10, 2018, now abandoned.

(51) Int. Cl.
| | | |
|---|---|---|
| *A61K 31/7042* | (2006.01) | |
| *A61K 9/28* | (2006.01) | |
| *A61K 9/20* | (2006.01) | |

(52) U.S. Cl.
CPC ........ *A61K 31/7042* (2013.01); *A61K 9/2018* (2013.01); *A61K 9/2054* (2013.01); *A61K 9/2866* (2013.01)

(58) Field of Classification Search
CPC .............. A61K 31/7042; A61K 9/2018; A61K 9/2054; A61K 9/2866
See application file for complete search history.

(56) References Cited

U.S. PATENT DOCUMENTS

| | | | | |
|---|---|---|---|---|
| 8,563,035 | B2 * | 10/2013 | Cifter | A61K 9/2893 |
| | | | | 424/468 |
| 8,999,941 | B2 | 4/2015 | Henschke et al. | |
| 2007/0155664 | A1 * | 7/2007 | Ranklove | A61K 9/5084 |
| | | | | 424/464 |
| 2013/0052266 | A1 | 2/2013 | Sugimoto et al. | |
| 2015/0005244 | A1 | 1/2015 | Wang et al. | |
| 2015/0343603 | A1 * | 12/2015 | Breder | B24D 11/00 |
| | | | | 451/28 |
| 2016/0002275 | A1 | 1/2016 | Desai et al. | |
| 2017/0105987 | A1 * | 4/2017 | Aberg | A61K 9/06 |

FOREIGN PATENT DOCUMENTS

| | | | | |
|---|---|---|---|---|
| CN | 104119323 A | 10/2014 | | |
| CN | 104402946 B | 1/2018 | | |
| CN | 103655539 B | 9/2019 | | |
| EP | 2990029 A1 * | 3/2016 | ............. | A61J 1/035 |
| WO | WO 2013064909 A2 | 5/2013 | | |
| WO | WO 2014195966 A2 | 12/2014 | | |
| WO | WO-2015142178 A1 * | 9/2015 | ........... | A61K 31/575 |
| WO | WO 2016030502 A1 | 3/2016 | | |

OTHER PUBLICATIONS

Gamble et al. "Investigation into the Degree of Variability in the Solid-State Properties of Common Pharmaceutical Excipients—Anhydrous lactose" in AAPS PharmSciTech, vol. 11, No. 4, Dec. 2010. (Year: 2010).*
Process for the preparation of amorphous Canagliflozin IP.com Published on Jun. 3, 2015 Refer Abstract and Examples.

* cited by examiner

*Primary Examiner* — Blessing M Fubara
(74) *Attorney, Agent, or Firm* — Jay R Akhave; PatentScience LLC (57) ABSTRACT

The present invention relates to a binder free stable pharmaceutical composition comprising amorphous canagliflozin or a pharmaceutically acceptable salt or a prodrug thereof, and one or more pharmaceutically acceptable excipients, wherein the said composition is devoid of canagliflozin hemihydrate, and having acceptable chemical stability, polymorphic stability & comparative dissolution and bioavailability profile to that of INVOKANA® tablets.

4 Claims, 2 Drawing Sheets

PHARMACEUTICAL COMPOSITION COMPRISING CANAGLIFLOZIN, PROCESS OF PREPARATION AND USE THEREOF

CROSS REFERENCE TO RELATED APPLICATIONS

This application claims the earliest priority from an Indian Patent Application IN 201641008349 filed on Mar. 10, 2016 and continuation-in-part of Ser. No. 16/083,534 filed on Sep. 10, 2018.

FIELD OF THE INVENTION

The present invention relates to a pharmaceutical composition comprising inhibitors of sodium-dependent glucose transporter and process of preparation thereof.

The present invention relates to a pharmaceutical composition comprising Canagliflozin or a prodrug or a pharmaceutically acceptable salt thereof and process of preparation thereof.

The present invention relates to a binder free stable pharmaceutical composition comprising of amorphous canagliflozin or a pharmaceutically acceptable salt or a prodrug thereof, wherein the said composition is devoid of canagliflozin hemihydrate, and process of preparation thereof.

The present invention also relates to binder free stable pharmaceutical composition comprising of amorphous canagliflozin or a pharmaceutically acceptable salt or a prodrug thereof, wherein the said composition is devoid of canagliflozin hemihydrate, for use in the treatment of diabetes mellitus, obesity, diabetic complications, and the like.

BACKGROUND OF THE INVENTION

WO 2005/012326 discloses a class of compounds that are inhibitors of sodium-dependent glucose transporter (SGLT) and thus of therapeutic use for treatment of diabetes, obesity, diabetic complications, and the like. U.S. Pat. No. 7,943,788 patent covers canagliflozin specific compound (A1).

U.S. Pat. No. 8,222,219 discloses the method of treatment of diabetes related condition such as a method for treating or delaying the progression or onset of a disease selected from diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, and hypertension, which comprises administering to a mammalian species in need of treatment a therapeutically effective amount of a compound of Formula (I).

WO 2005/012326 describes 14.beta.-D-glucopyranosyl)-4-methyl-3-[5-(4-fluoro-phenyl)-2-thienylmeth-yl] benzene having the following formula: (A)

Compound (A) hemihydrate and a certain crystal form thereof are disclosed in International Patent Application WO 2008/069327.

INVOKANA® (Canagliflozin) tablets 100 mg & 300 mg got approved in the USA market on Mar. 29, 2013. INVOKANA is a sodium-glucose co-transporter 2 (SGLT2) inhibitor indicated as an adjunct to diet and exercise to improve glycemic control in adults with type 2 diabetes mellitus. Inactive ingredients of INVOKANA core tablet are croscarmellose sodium, hydroxypropyl cellulose, lactose anhydrous, magnesium stearate, and microcrystalline cellulose. The magnesium stearate is vegetable-sourced. The tablets are finished with a commercially available film-coating consisting of the following excipients: polyvinyl alcohol (partially hydrolyzed), titanium dioxide, macrogol/PEG, talc, and iron oxide yellow, E172 (100 mg tablet only).

US 2015/0005244 of Janssen Pharmaceutica covers an orally administrable pharmaceutical tablet comprising:
(a) a compound of 1-((3-D-gluco-pyranosyl)-3-(phenylthienylmethyl) benzene derivative or a prodrug or pharmaceutically acceptable salt thereof present in an amount within the range of from about 40% to about 60% by weight;
(b) a diluent or filler comprising a combination of microcrystalline cellulose and lactose present in an amount within the range of from about 30% to about 50% by weight; (c) croscarmellose sodium in an amount within the range of from about 3% to about 10% by weight;
(d) hydroxypropyl cellulose present in an amount within the range of from about 0.5% to about 5% by weight; and (e) magnesium stearate present in an amount within the range of from about 0.5% to about 2% by weight; wherein the % by weight is based on the weight of the tablet.

US 2013/0052266 of Mitsubishi Tanabe Pharma Corporation covers a tablet comprising a compound of formula (A) (canagliflozin) or a pharmaceutically acceptable salt thereof, a lubricant, and one or more pharmaceutically acceptable additives, wherein compound (A) or a pharmaceutically acceptable salt thereof is present in an amount within the range of from about to 95% by weight of tablet, and wherein the lubricant is talc and sodium stearyl fumarate.

U.S. Pat. No. 7,943,582 (IN 3871/CHENP/2009) of Mitsubishi Tanabe Pharma Corporation discloses crystalline Canagliflozin hemihydrate. This patent also discloses the preparation of Canagliflozin hemihydrate, by crystallizing Canagliflozin from a good solvent and water, optionally containing a poor solvent; wherein the good solvent is selected from ketones, esters, alcohols and a mixture of these solvents; poor solvent is selected from alkanes, aromatic hydrocarbons, ethers and a mixture of these solvents. US '582 also stated that Canagliflozin prepared according to the process described in the PCT application WO 2005/012326 (U.S. Pat. No. 7,943,788) yields Canagliflozin in the amorphous form.

US 2012/0289694 of Nguyen discloses L-proline and citric acid co-crystals of Canagliflozin.

US 2013/0237487 of Scinopharm Taiwan, Ltd discloses Canagliflozin Form CS1 (Canagliflozin L-proline complex), CS2 (Canagliflozin D-proline complex), CS3 (Canagliflozin L-phenylalanine complex), CS4 (Canagliflozin D-proline complex) and CS5. This patent also discloses a process for the preparation of amorphous Canagliflozin, which comprises, dissolving Canagliflozin in toluene with heating and addition of this solution to n-heptane.

WO 2016/206660 of Zentiva discloses a solid solution of amorphous canagliflozin, characterized in that it contains at least one pharmaceutically acceptable excipient. This patent also discloses that for stabilization of the amorphous form of canagliflozin, solid compositions (solid dispersions, amorphous solid dispersions or solid solutions) with polymers, copolymers, saccharides, oligosaccharides, polysaccharides, fats, waxes or urea, preferably especially with polymers, can be used.

US 2016/0083374 of Cadila Healthcare Limited discloses a stable amorphous form of canagliflozin, wherein the amorphous canagliflozin does not convert to any other solid form when stored at a temperature of up to about 40° C. and at a relative humidity of about 25% to about 75% for about three months or more. This patent also discloses an amorphous form of Canagliflozin having purity by HPLC greater than 99% and residual solvent less than 0.5%.

WO 2016/030502 of Sandoz AG discloses a formulation comprising a non-stoichiometric hydrate of Canagliflozin or an amorphous Canagliflozin, and at least one of excipients, wherein the formulation is defined by a water activity of <0.3, determined at room temperature.

Canagliflozin is a poorly soluble compound with incomplete bioavailability. Poor drug solubility however represents a bottleneck for dissolution, which in turn critically affects drug bioavailability. In order to overcome dissolution and bioavailability constraints, the currently marketed formulation of Canagliflozin (INVOKANA®) contains Canagliflozin as a hemihydrate form along with a diluent, a disintegrant, a binder and a lubricant. Aforementioned prior art document US 2015/0005244 of Janssen covers Canagliflozin formulations comprising about 40% to about 60% by weight of Canagliflozin, binder, disintegrant & lubricant. Canagliflozin is also susceptible to chemical stability and exists in various solid forms with different pharmacological and toxicological behaviors, and with variable bioavailabilties. WO2016/030502 of Sandoz covers Canagliflozin formulations with a water activity of <0.3. However, such formulations can be manufactured only by 'Dry-method", and requires cumbersome and costly process steps such as setting up an area with very low RH condition during manufacturing and prior drying of excipients before making the formulation.

Therefore, none of the above prior art documents discloses simple and cost-effective canagliflozin formulations which can be prepared by simple manufacturing processes, and wherein such compositions have acceptable chemical stability, polymorphic stability & comparative dissolution and bioavailability profile to that of INVOKANA® tablets, thereby achieving target therapeutic effect, when administered to the patients.

Surprisingly, the present invention relates to novel amorphous canagliflozin formulations and process of preparation thereof. The present invention provides a binder free stable pharmaceutical composition comprising amorphous canagliflozin or a pharmaceutically acceptable salt or a prodrug thereof, and one or more pharmaceutically acceptable excipients, wherein the said composition is devoid of canagliflozin hemihydrate, and having acceptable chemical stability, polymorphic stability & comparative dissolution and bioavailability profile to that of INVOKANA® tablets.

SUMMARY OF INVENTION

Aspects of the present invention relates to pharmaceutical compositions comprising of canagliflozin or a pharmaceutically acceptable salt or a prodrug thereof along with one or more pharmaceutically acceptable excipients.

Aspects of the present invention relates to a binder free stable pharmaceutical composition comprising of amorphous canagliflozin or a pharmaceutically acceptable salt or a prodrug thereof, and one or more pharmaceutically acceptable excipients, wherein the said composition is devoid of canagliflozin hemihydrate.

Aspects of the present invention relate to a binder free stable pharmaceutical composition comprising of: (a) amorphous canagliflozin or a pharmaceutically acceptable salt or a prodrug thereof; (b) a diluent or filler; (c) a disintegrant; (d) a lubricant, and (e) a surfactant, wherein the said composition is devoid of canagliflozin hemihydrate.

Aspects of the present invention relate to a binder free stable pharmaceutical composition comprising of:
  (a) amorphous canagliflozin or a pharmaceutically acceptable salt or a prodrug thereof, present in an amount within the range of from about 5% to about 70% by weight;
  (b) a diluent or filler comprising a combination of microcrystalline cellulose and lactose present in an amount within the range of from about 5% to about 90% by weight;
  (c) a disintegrant in an amount within the range of from about 1% to about 30% by weight
  (d) a surfactant in an amount within the range of from about 1% to about 10% by weight and;
  (e) a lubricant present in an amount within the range of from about 0.25% to about 5% by weight; wherein the % by weight is based on the weight of the tablet; and the said composition is devoid of canagliflozin hemihydrate.

Aspects of the present invention also relate to a process of preparation of binder free stable pharmaceutical composition comprising of amorphous canagliflozin or a pharmaceutically acceptable salt or a prodrug thereof along with one or more pharmaceutically acceptable excipients, wherein the said composition is devoid of canagliflozin hemihydrate.

Aspects of the present invention relate to a binder free stable pharmaceutical composition comprising of amorphous canagliflozin or a pharmaceutically acceptable salt or a prodrug thereof, wherein the said composition is devoid of canagliflozin hemihydrate, for use in the treatment of one or more of diabetes mellitus, obesity, diabetic complications, and related diseases or disorders.

BRIEF DESCRIPTION OF THE DRAWINGS

FIG. 1 illustrates the X-ray powder diffraction pattern of the following:
I. indicates the X-ray powder diffraction pattern of placebo of example 3A.
II. indicates the X-ray powder diffraction pattern of Canagliflozin tablets of example 3 stored at 40±2° C./75±5% RH for 3 months in HDPE bottle having 2 gram silica gel+2 gram Molecular Sieve.
III. indicates the X-ray powder diffraction pattern of Canagliflozin tablets of example 3 stored at 30±2° C./65±5% RH for 3 months in HDPE bottle having 2 gram silica gel+2 gram Molecular Sieve.
IV. indicates the X-ray powder diffraction pattern of tablets prepared according to example 3 at initial stage.
V. indicates the X-ray powder diffraction pattern of Canagliflozin hemihydrate (Standard).
VI. indicates the X-ray powder diffraction pattern of input API [Amorphous Canagliflozin API (Micronized)].

DETAILED DESCRIPTION OF THE INVENTION

As used herein, "a" or "an" means one or more unless otherwise specified. Open terms such as "include," "including," "contain," "containing" and the like mean "comprising".

The term "treatment" or "treating" refers to administering a therapy in an amount, manner, or mode effective to improve a condition, symptom, or parameter associated with a disorder.

The term "Administering" or "administration" means providing a drug to a patient in a manner that is pharmacologically useful.

The term "Patient" or "subject" means an animal, preferably a mammal, more preferably human, in need of therapeutic intervention.

The term "Dosage form" means one or more compounds in a medium, carrier, vehicle, or device suitable for administration to a patient. "Oral dosage form" means a dosage form suitable for oral administration.

The term "or" can be conjunctive or disjunctive.

The term "% by weight" is based on the weight of the tablet.

The term "composition" is intended to encompass a product comprising the specified ingredients in the specified amounts, as well as any product which results, directly or indirectly, from combinations of the specified ingredients in the specified amounts.

The term "prodrug" means an ester or carbonate, or any other form which can get converted at least substantially into canagliflozin particularly upon in-vivo administration.

The term "pharmaceutically acceptable" means molecular entities and compositions that are of sufficient purity and quality for use in the formulation of a composition or medicament of the present invention. Since both human use (clinical and over-the-counter) and veterinary use are equally included within the scope of the present invention, a formulation would include a composition or medicament for either human or veterinary use.

The term "pharmaceutically acceptable salt" refers includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl) aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The term "related substance", as used herein, is to denote certain process and/or degradation related impurities, which could be formed during manufacture and/or storage of the API, and during manufacture and/or storage of a pharmaceutical composition containing the API.

The term "Dissolution" means process in which a substance forms a solution. Dissolution testing measures the extent and rate of solution formation from a dosage form, such as tablet, capsule, ointment, etc. The dissolution of a drug is important for its bioavailability and therapeutic effectiveness. Dissolution testing is routinely carried out in the pharmaceutical industry to determine the rate of dissolution of solid dosage forms. In addition to being routinely used by pharmaceutical companies to demonstrate adequate drug release in vivo, in vitro dissolution testing is used to assist with formulation design, process development, and especially the demonstration of batch-to-batch reproducibility in production. Dissolution testing is one of several tests that pharmaceutical companies typically conduct on oral dosage formulations (e.g., tablets, capsules, etc) to determine compliance and to release products for distribution and sales.

The term "discriminative dissolution medium" means any dissolution medium which has the discriminatory power of the dissolution method and ability to detect changes in the drug product performance, generally demonstrated by determining the effect of deliberate changes in the formulation or process on dissolution characteristics. A discriminating medium is one part of discriminating dissolution test. The media should be able to meet sink condition. To determine a good media typically it is but to select study several different pH media, rpm. The dissolution method should be sensitive to variation that can be an impact on the in vivo performance of the dosage form. Discriminative method is found to be promising tool for the new drug in the selection of better medium based upon its physico-chemical nature with respect to the body condition.

In one of the particular embodiments the discriminating dissolution medium employed for the invention compositions was 0.25% Tween 80 in 600 mL of water at 50 rpm with USP Apparatus II (Paddle) using sampling times 5, 10, 15, 20, 30, 45 & 60 Minutes.

The term "non discriminative dissolution medium" means any dissolution medium which has no discriminatory power to detect changes in the drug product performance in the dissolution method.

In one of the particular embodiments the non discriminating dissolution medium employed for the invention compositions was 0.75% sodium lauryl sulphate in 600 mL of water at 75 rpm with USP Apparatus II (Paddle) using sampling times 5, 10, 15, 20, 30, 45 & 60 minutes The term "stable" or "stability" as used herein refers to a pharmaceutical composition that retains its physical stability, polymorphic stability and/or chemical stability and comply with the standard stability criteria given in USP compendia.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations of +/-10% to the actual given value due to experimental and/or measurement conditions for such given value.

In embodiments, the present invention provides a binder free stable pharmaceutical composition comprising of amorphous canagliflozin or a pharmaceutically acceptable salt or a prodrug thereof, and one or more pharmaceutically acceptable excipients, wherein the said composition is devoid of canagliflozin hemihydrate.

In certain embodiments of the present invention the formulation includes an amorphous Canagliflozin disclosed in Patent Application No. 1978/CHE/2014 which is incorporated herein by reference in its entirety. WO 2014/195966 discloses a process for the preparation of amorphous form of Canagliflozin by spray drying, agitated thin film drying ("ATFD"), and freeze drying (lyophilization).

Typically, the amorphous canagliflozin is sieved and/or milled to control its particle size. In a preferred embodiment the Canagliflozin has a particle size distribution of d (50) of not more than (NMT) 150 µm or d (50) NMT 80 µm; and d (90) NMT 250 µm or d (90) NMT 150 µm measured using the laser diffraction particle size analyzer such as Mastersizer 2000 (Malvern Instruments).

The oral dosage form may be provided in any pharmaceutically acceptable solid dosage form. Preferably, the solid dosage form includes, for example, solid preparation such as tablets, pills, granules, capsules, powders and others. In embodiments, the solid dosage form is an oral tablet or capsule formulation. In an embodiment, the solid dosage form is an oral tablet.

In embodiments, the present invention provides a binder free stable tablet composition comprising of (a) amorphous canagliflozin or a pharmaceutically acceptable salt or a prodrug thereof; (b) a diluent or filler; (c) disintegrant; (d) lubricant and (e) surfactant, wherein the said composition is devoid of canagliflozin hemihydrate.

The tablet of the present invention may contain additives generally used in pharmaceutical solid tablets. Examples of the additives include bulking agents (diluents or fillers), disintegrants, lubricants, coating agents, surfactants, flavors, colorants and sweetening agents.

In certain embodiments of the present invention the formulation includes a filler or diluent in the amount of about 5% to about 95% by weight of the formulation or from about 20% to about 60% by weight of the formulation.

Examples of the diluents or fillers suitable for use herein include lactose, sucrose, mannitol, xylitol, erythritol, sorbitol, maltitol, calcium citrate, calcium phosphate, and calcium aluminometasilicate. Examples of the bulking agents or fillers also include cellulose derivatives, such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, and compressible sugars. And mixtures of two or more above bulking agents or fillers can be used also. Combination of microcrystalline cellulose and lactose is particularly suitable for use in the tablet of the present invention.

In certain embodiments of the present invention the formulation includes a disintegrant in the amount of about 0.1% to about 20% by weight of the formulation, or from about 0.25% to about 15% by weight of the formulation.

Examples of disintegrants suitable for use herein include croscarmellose sodium, crospovidone, starch, potato starch, pregelatinized starch, corn starch, sodium starch glycolate, microcrystalline cellulose, low substituted hydroxypropyl cellulose and other known disintegrants. In an embodiment, the disintegrant used in the tablet is croscarmellose sodium.

In certain embodiments of the present invention the formulation includes a lubricant in the amount of about 0.25% to about 5% by weight of the formulation, or from about 0.1% to about 2% by weight of the formulation.

Examples of lubricants suitable for use herein include magnesium stearate, zinc stearate, calcium stearate, talc, carnauba wax, stearic acid, palmitic acid, sodium stearyl fumarate, sodium laurel sulfate, glyceryl palmitostearate, palmitic acid, myristic acid and hydrogenated vegetable oils and fats. In an embodiment, the lubricant suitable for use herein is magnesium stearate.

In certain embodiments of the present invention the formulation includes a surfactant in the amount of about 0.1% to about 20% by weight of the formulation, or from about 0.25% to about 10% by weight of the formulation. Surfactants for use in the formulations of the present invention include surfactants commonly used in the formulation of pharmaceuticals.

Examples of surfactants for use in accordance with the present invention include but are not limited to ionic- and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium lauryl sulfate, cholic acid or derivatives thereof, lecithins, phospholipids, combinations thereof, and the like. In an embodiment, the Surfactant suitable for use herein is polysorbate 80.

In embodiments, the present invention provides a binder free stable pharmaceutical composition comprising:
 (a) canagliflozin or a prodrug or pharmaceutically acceptable salt thereof, present in an amount within the range of from about 5% to about 70% by weight;
 (b) a diluent or filler comprising a combination of microcrystalline cellulose and lactose present in an amount within the range of from about 5% to about 90% by weight;
 (c) a disintegrant in an amount within the range of from about 1% to about 30% by weight and
 (d) a surfactant in an amount within the range of from about 1% to about 10% by weight and;
 (e) a lubricant present in an amount within the range of from about 0.025% to about 5% by weight; wherein the % by weight is based on the weight of the tablet; and the said composition is devoid of canagliflozin hemihydrate.

In certain embodiments, the present invention provides a binder free stable pharmaceutical composition comprising:

(a) canagliflozin or a prodrug or pharmaceutically acceptable salt thereof, present in an amount within the range of from about 30% to about 50% by weight;
(b) a diluent or filler comprising a combination of microcrystalline cellulose and lactose present in an amount within the range of from about 30% to about 50% by weight;
(c) a croscarmellose sodium in an amount within the range of from about 10% to about 20% by weight and
(d) a polysorbate 80 in an amount within the range of from about 1% to about 3% by weight and;
(e) a lubricant present in an amount within the range of from about 0.5% to about 2% by weight; wherein the % by weight is based on the weight of the tablet; and the said composition is devoid of canagliflozin hemihydrate.

In certain embodiments, the present invention provides a binder free stable pharmaceutical composition e prepared by the process comprising of: (a) forming granules of pharmaceutically acceptable excipients in Fluid bed processor, (b) mixing the granules thus obtained together with canagliflozin and other pharmaceutically acceptable excipients, (c) forming the slug of step (b) by passing through roller compactor, (d) obtaining granules by passing slug of step (c) through oscillating granulator, (e) mixing other pharmaceutically acceptable excipients to the obtained granules of step (d), (f) forming the tablet by compressing the mixture obtained in step (e), and (g) coating the tablet.

In certain embodiments, the present invention provides a binder free stable pharmaceutical composition comprising of amorphous canagliflozin or a pharmaceutically acceptable salt or a prodrug thereof, and one or more pharmaceutically acceptable excipients, wherein the said composition is prepared by a process comprising the following steps: (a) forming granules of pharmaceutically acceptable excipients in Fluid bed processor; (b) mixing the granules thus obtained together with canagliflozin and other pharmaceutically acceptable excipients; (c) forming the slugs of step (b); (d) milling the slugs of step (c); (e) mixing other pharmaceutically acceptable excipients to the obtained granules of step (d); (f) forming the tablet by compressing the mixture obtained in step (e); (g) Optionally coating the tablet;

In another embodiment, the tablet or capsule of the invention has a protective outer layer. The protective outer layer of the tablet or capsule, where present, can include from about 5% to about 95% of polymer based on the weight of the coating layer, and can be prepared employing conventional procedures. In one embodiment, the outer layer of the tablet or capsule includes from about 20% to about 90% of polymer based on the weight of the coating layer. The formulation can contain at least one coating layer polymer and a coating solvent, for example, water, which is used for processing and removed by drying. Suitable examples of polymer for the coating layer include, but are not limited to, hydroxypropyl methylcellulose, polyvinyl alcohol (PVA), ethyl cellulose, methacrylic polymers, hydroxypropyl cellulose, and starch. In one embodiment, the coating layer polymer is PVA. In another embodiment, the coating layer polymer is hydroxypropyl cellulose.

The coating can also optionally include a plasticizer of from about 0% to about 30% by weight, based on the weight of the coating layer. In one embodiment, the plasticizer is from about 10% to about 25% by weight of the coating layer. Suitable plasticizers include, but are not limited to, triacetin, diethyl phthalate, tributyl sebacate, polyethylene glycol (PEG), glycerin, triacetin, and triethyl citrate.

In another embodiment, the coating can also optionally include an anti-adherent or glidant such as talc, fumed silica, or magnesium stearate.

In another embodiment, the coating can also optionally include an opacifying agent, such as titanium dioxide.

In yet another embodiment, wherein the formulation is a tablet, the tablet may be further coated with a coating layer that provides cosmetic benefits to the dosage form. In certain embodiments, such a coating helps to protect the tablets. In certain embodiments such coating comprises hydroxypropyl methylcellulose, polyethylene glycol, polydextrose, titanium dioxide, and triacetin. In certain other embodiments such coating comprises hydroxypropyl methylcellulose 2910, polyethylene glycol 400, polydextrose, titanium dioxide, carnuba wax, and iron oxide yellow. In at least one embodiment such a coating layer comprises Opadry II (white) in an amount of from about 0% to about 10% by weight of the tablet; in certain other embodiments in an amount of from about 0% to about 6% by weight of the tablet; and in still other embodiments in an amount of from about, 0% to about 3% by weight of the tablet; and in other embodiments from about 2 to about 4% by weight of the tablet.

In certain embodiments of the present invention provides a binder free stable pharmaceutical formulation comprising of amorphous canagliflozin or a pharmaceutically acceptable salt a prodrug thereof, and one or more pharmaceutically acceptable excipients, wherein the said composition is devoid of canagliflozin hemihydrate, and the formulation includes controlled amounts of related substances (Impurities).

In certain embodiments of the present invention provides a binder free stable pharmaceutical formulation comprising of amorphous canagliflozin or a pharmaceutically acceptable salt a prodrug thereof, and one or more pharmaceutically acceptable excipients, wherein the said composition is devoid of canagliflozin hemihydrate, and the formulation comprises less than 0.2% of related substances (known impurities) such as Desfluoro canagliflozin, Methoxy canagliflozin, Bromo Rhiphene; 0.2% of unknown impurities; and 1% of total impurities.

The following examples are intended to serve as illustrations of the present invention only and do not restrict the scope of the invention in any manner whatsoever.

Example 1 & 2

| Ingredients | Example 1 Qty/tablet (mg) | Example 2 Qty/tablet (mg) |
| --- | --- | --- |
| Intragranular part | | |
| Amorphous Canagliflozin | 300.00 | 300.00 |
| Lactose | 15.00 | 132.00 |
| Microcrystalline cellulose | 100.00 | 126.00 |
| Croscarmellose sodium | 45.00 | 15.00 |
| Magnesium stearate | 3.00 | 3.00 |
| Sodium Lauryl Sulfate (SLS) | — | 6.00 |
| Extragranular part | | |
| Lactose | 55.00 | — |
| Microcrystalline cellulose | 34.00 | — |
| Croscarmellose sodium | 45.00 | 15.00 |
| Magnesium stearate | 3.00 | 3.00 |
| Core tablet | 600.00 | 600.00 |
| Opadry ® II 85F18422 | 18.00 | 18.00 |
| Coated tablet | 618.00 | 618.00 |

Opadry ® II 85F18422 contains: Polyvinyl alcohol (Partially hydrolyzed), Macrogol/PEG 3350, Titanium dioxide and Talc.

Manufacturing Procedure for Canagliflozin Tablets 300 mg of Examples 1 & 2:

Intragranular Part:

Step 1: Lactose, microcrystalline cellulose, SLS (For Example 2) and croscarmellose sodium were co-sifted through a sieve.

Step 2: Canagliflozin was mixed with co-sifted material of Step-1 and passed through a sieve.

Step 3: Step-2 material was mixed in blender.

Step 4: Magnesium stearate was sifted separately and mixed with the Step-3 material.

Step 5: The dry mix blend of Step-4 was passed through roller compactor and slugs were collected.

Step 6: The slugs of Step-5 were milled through Oscillating Granulator with a suitable screen and finally sifted through a sieve.

Extragranular Part:

Step 7: Lactose, microcrystalline cellulose and croscarmellose sodium (only one extragranular excipient for Example 2) were co-sifted and added to the sifted material of Step-6 and mixed.

Step 8: Magnesium stearate was sifted and added to Step-7 material and mixed.

Tablet:

Step 9: The lubricated blend of Step-8 was compressed into tablets.

Step 10: The core tablets of Step-9 were coated with 10% aqueous dispersion of Opadry® II 85F18422 for a weight build-up of about 2-5% w/w.

Step 4: Co-sifted microcrystalline cellulose, dummy granules of step 3 and Croscarmellose sodium through suitable sieve Step 5: Co-sifted canagliflozin through suitable sieve Step 6: materials of step 4 & 5 and loaded in to a blender.

Step 7: Magnesium stearate was sifted separately and mixed with the Step-6 material.

Step 8: Unloaded the lubricated granules of step 7 and passed the materials through roller compactor to make the slug Step 9: Milled the slug through oscillating granulator with suitable screen and finally sift through suitable sieve.

Step 10: To the sifted granules, croscarmellose sodium was added and mixed through suitable blender.

Step 11: To the above blend magnesium stearate was added and mixed.

Step 12: Compressed the above lubricated blend by using suitable tablet tooling.

Step 13: Dispersed Opadry white in purified water; continued stirring till the end of coating process and above compressed tablets were coated up to and 3-4% weight build up.

Figure 1:
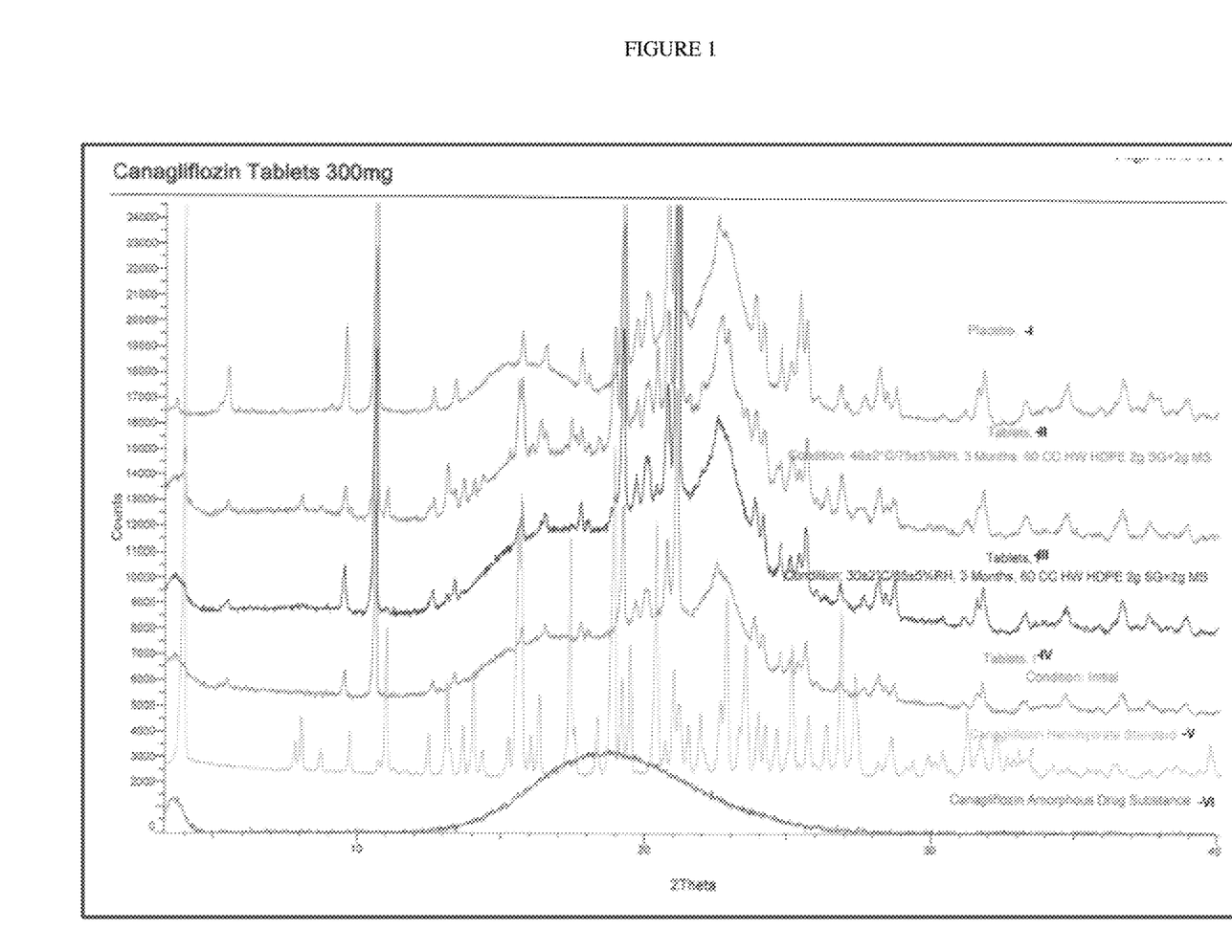

Manufacturing Procedure for Placebo Tablets for Canagliflozin Tablets 300 mg of Example 3A:

Example 3A are the Placebo Tablets for Example 3, which was prepared according to the manufacturing process of example 3 with the exclusion of canagliflozin in the composition. The polymorphic characterization of placebo tablets were done (Refer to FIG. 1).

Example 3

| Ingredients | EXAMPLE 3 Quantity (mg/Tab) | EXAMPLE 3A Quantity (mg/Tab) |
|---|---|---|
| Dry mix and Granulation (Part-1) | | |
| Lactose Anhydrous | 99.05 | 99.05 |
| Microcrystalline Cellulose | 99.05 | 99.05 |
| Polysorbate 80 | 13.20 | 13.20 |
| Purified Water | q.s. | q.s. |
| Compaction (Part -2) | | |
| Part-1 Granules | 230.00 | 230.00 |
| Canagliflozin | 300.00 | — |
| Microcrystalline Cellulose | 34.00 | 34.00 |
| Cros-carmellose sodium | 45.00 | 45.00 |
| Magnesium Stearate | 3.00 | 3.00 |
| Blending | | |
| Cros-carmellose sodium | 45.00 | 45.00 |
| Lubrication | | |
| Magnesium Stearate | 3.00 | 3.00 |
| Core Tablet Weight | 660.00 | 360.00 |
| Film coating | | |
| Opadry II White | 19.80 | 19.80 |
| Purified Water | q. s. | q. s. |
| Coated Tablet Weight | 679.80 | 379.8 | q.s: Quantity Sufficient

Manufacturing Procedure for Canagliflozin Tablets 300 mg of Examples 3:

Step 1: Lactose anhydrous and microcrystalline cellulose were shifted together through suitable sieve.

Step 2: Polysorbate 80 was dissolved in required purified water with constant stirring to get clear solution.

Step 3: The blend of Step-1 material was granulated with step 2 material i.e. polysorbate-80 surfactant solution and dried the granules at bed temperature.

Example 4

| Ingredients | EXAMPLE 4 Qty/Tablet (mg) | EXAMPLE 4A Qty/Tablet (mg) |
|---|---|---|
| Intragranular part for Fluid Bed Processer-FBP (Part-1) | | |
| Lactose Anhydrous | 117.75 | 117.75 |
| Microcrystalline Cellulose | 76.05 | 76.05 |
| Granulating Fluid-1 | | |
| Polysorbate 80 | 13.20 | 13.20 |
| Purified Water* | q.s. | q.s. |
| Granulating Fluid-2 | | |
| Lactose Anhydrous | 23.00 | 23.00 |
| Purified Water* | q.s. | q.s. |
| Intragranular part for compaction (Part-2) | | |
| Canagliflozin | 300.00 | — |
| Microcrystalline Cellulose | 34.00 | 34.00 |
| Croscarmellose Sodium | 45.00 | 45.00 |
| Magnesium stearate | 3.00 | 3.00 |
| Extragranular Part | | |
| Croscarmellose Sodium | 45.00 | 45.00 |
| Lubricant | | |
| Magnesium stearate | 3.00 | 3.00 |
| Core Tablet Weight | 660.00 | 360.00 |
| Coating | | |
| Opadry White | 19.80 | 19.80 |
| Total Weight | 679.80 | 379.80 |

*Processing solvent, not present in final product except traces.

Manufacturing Procedure:

Step 1: Lactose anhydrous and microcrystalline cellulose were shifted together through suitable sieve.

Step 2: Dissolved polysorbate 80 in required purified water with constant stirring to get clear solution.

Step 3: Filtered the step 2 solution to remove the lumps/aggregates.

Step 4: Dissolved the other part of lactose anhydrous in purified water with constant stirring to get clear solution.

Step 5: Filtered the step 4 solution to remove the lumps/aggregates.

Step 6: Sifted material of step 1 was loaded in to FBP and coated the materials using solution of step 2 and further continued coating with the solution of step 4 and after completion of spraying, dried the granules at bed temperature.

Step 7: Co-sifted microcrystalline cellulose, dummy granules of step 6 and Croscarmellose sodium through suitable sieve.

Step 8: Co-sifted canagliflozin and materials of step 7 through suitable sieve and loaded in to a blender.

Step 9: Added the sifted magnesium stearate to the step 8 and lubricated for fixed duration.

Step 10: Unloaded the lubricated granules of step 9 and passed the materials through roller compactor to make the slug.

Step 10: Milled the slug through oscillating granulator with suitable screen and finally sift through suitable sieve.

Step 11: To the sifted granules, croscarmellose sodium was added and mixed through suitable blender.

Step 12: To the above blend magnesium stearate was added and mixed.

Step 13: Compressed the above lubricated blend by using suitable tablet tooling.

Step 14: Dispersed opadry white in purified water; continued stirring till the end of coating process and above compressed tablets were coated up to and 3-4% weight build up.

Figure 2:
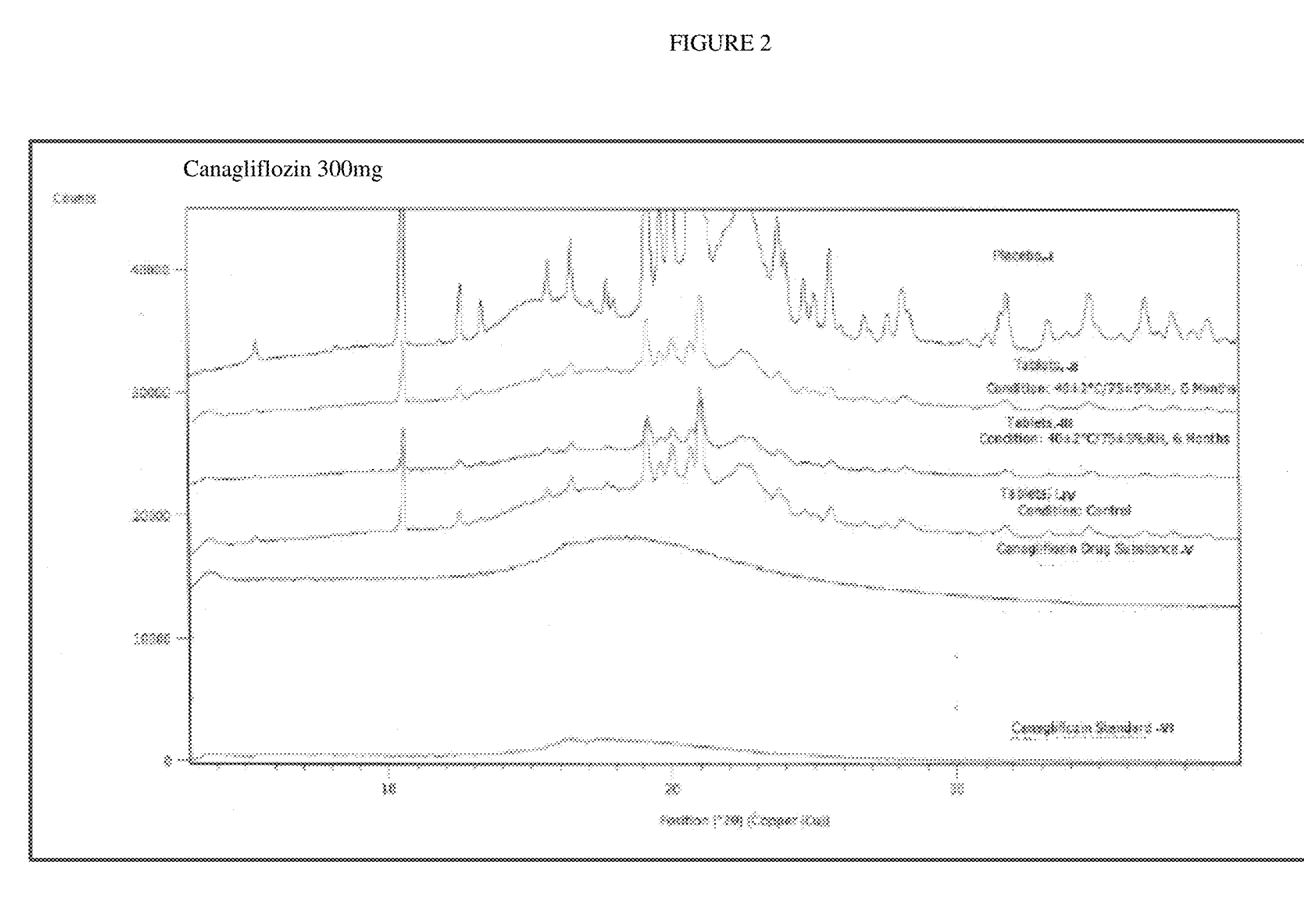
FIG. 2 illustrates the X-ray powder diffraction pattern of the following:
I. indicates the X-ray powder diffraction pattern of placebo of example 4A.
II. indicates the X-ray powder diffraction pattern of Canagliflozin tablets of example 4 stored at 40±2° C.175% RH for 6 months in HDPE bottle.
III. indicates the X-ray powder diffraction pattern of Canagliflozin tablets of example 4 stored at 40±2° C./75% RH for 6 months in HDPE bottle.
IV. indicates the X-ray powder diffraction pattern of tablets prepared according to example 4 at initial stage.
V. indicates the X-ray powder diffraction pattern of Amorphous Canagliflozin input API (Micronized).
VI. indicates the X-ray powder diffraction pattern of Canagliflozin API (Standard).

Manufacturing Procedure for Placebo Tablets for Canagliflozin Tablets 300 mg of Example 4A:

Example 4A are the Placebo Tablets for Example 4, which was prepared according to the manufacturing process of example 4 with the exclusion of canagliflozin in the composition. The polymorphic characterization of placebo tablets were done (Refer to FIG. 2).

The dissolution profile was determined in discriminating media for amorphous canagliflozin formulations of examples 1, 2, 3 & 4. It was concluded that dissolution profile of amorphous canagliflozin compositions of examples 1&2 (with or without sodium lauryl sulfate) were not comparable to dissolution profile of commercially available canagliflozin hemihydrate tablets. However, surprisingly it was concluded that dissolution profile of amorphous canagliflozin compositions of examples 3 & 4 (with polysorbate 80) were comparable to dissolution profile of commercially available canagliflozin hemihydrate tablets.

Dissolution Conditions:

Medium: 0.25% Tween 80 in water; 600 mL.
Method: Paddle (Apparatus II); 50 RPM.
Time intervals: 5, 10, 15, 20, 30, 45 & 60 Minutes.

| Time intervals (Minutes) | Example 1 | Example 2 | Example 3 | Example 4 | INVOKANA® Tablets |
|---|---|---|---|---|---|
| | % Drug released | | | | |
| 5 | 20 | 22 | 30 | 34 | 25 |
| 10 | 33 | 39 | 52 | 67 | 53 |
| 15 | 50 | 51 | 63 | 83 | 68 |
| 20 | 56 | 55 | 70 | 88 | 76 |
| 30 | 64 | 67 | 78 | 90 | 83 |
| 45 | 70 | 73 | 84 | 92 | 88 |
| 60 | 76 | 77 | 89 | 93 | 92 |

The dissolution profile was determined in non-discriminating media for amorphous canagliflozin formulations of examples 3 & 4. Between these two formulations it was concluded that dissolution profile of amorphous canagliflozin compositions of examples 4 (with polysorbate 80 prepared by fluid bed processer) were comparable to dissolution profile of commercially available canagliflozin hemihydrate tablets.

Dissolution Profile:

Medium: 0.75% Sodium lauryl sulphate in water; 600 mL.
Method: Paddle (Apparatus II); 75 RPM.
Time intervals: 5, 10, 15, 20, 30, 45 & 60 Minutes.

| Time intervals (Minutes) | Example 3 | Example 4 | INVOKANA® Tablets |
|---|---|---|---|
| | % Drug released | | |
| 5 | 58 | 35 | 41 |
| 10 | 93 | 67 | 70 |
| 15 | 99 | 87 | 89 |
| 20 | 100 | 97 | 93 |
| 30 | 100 | 98 | 96 |
| 45 | 101 | 100 | 99 |
| 60 | 101 | 100 | 100 |

Chemical stability data was determined for amorphous canagliflozin formulations of example 4:—

| | % w/w of Related substances at Initial stage | | | | |
|---|---|---|---|---|---|
| Sample | Desfluoro Canagliflozin | Methoxy Canagliflozin | Bromo thiophene | Maximum Unknown | Total impurity |
| Example 4 | 0.02 | 0.00 | 0.00 | 0.03 | 0.08 |

| | % w/w of Related substances at 40° C./75% RH 3 Months | | | | |
|---|---|---|---|---|---|
| Sample | Desfluoro Canagliflozin | Methoxy Canagliflozin | Bromo thiophene | Maximum Unknown | Total impurity |
| Example 4 | 0.02 | 0.01 | 0.00 | 0.04 | 0.08 |

Polymorphic Stability:

Note: Input canagliflozin used for manufacture of aforementioned example 3 & 4 is amorphous canagliflozin.

| Time | Example 3 |
|---|---|
| Initial | Amorphous (FIG. 1) |
| 30 ± 2° C./ 65 ± 5% RH; 3 Months | About 2% hemihydrate and amorphous form (FIG. 1) |
| 40 ± 2° C./ 75 ± 5% RH; 3 Months | About 6% hemihydrate and amorphous form (FIG. 1) |

| Time | Example 4 |
|---|---|
| Initial | Amorphous (FIG. 2) |
| 40 ± 2° C./ 75 ± 5% RH; 6 Months | Amorphous (FIG. 2) |

Summary and conclusion:

| Experiments | Comparison of dissolution results with that of Canagliflozin hemihydrate tablets | Comparative Bioavailability results with that of Canagliflozin hemihydrate tablets [Cmax, AUC(0-t)& AUC(0-Infinity)] | Polymorphic results | Conclusions |
| --- | --- | --- | --- | --- |
| Example 3 | Discriminating dissolution media: - comparable. Non-discriminating dissolution media: - comparable. | Fasting state: Comparable. Fed state: Cmax on lower side. | polymorphic conversion was observed | Not satisfactory |
| Example 4 | Discriminating dissolution media: - more comparable. Non-discriminating dissolution media: - comparable. | Fasting state: Comparable Fed state: Comparable | Amorphous canagliflozin got retained in the finished product. | Satisfactory and unexpected findings. |

We claim:

1. A stable pharmaceutical composition consisting of amorphous canagliflozin, lactose, microcrystalline cellulose, polysorbate 80, croscarmellose sodium and magnesium stearate; wherein the said amorphous canagliflozin composition is devoid of canagliflozin hemihydrate and stable for at least 6 months in 40° C./75% RH and has a comparable bioavailability with the commercially available canagliflozin hemihydrate tablets, wherein the composition is prepared by fluidized bed processor using two granulating fluids.

2. The pharmaceutical composition according to claim 1, consisting 30-50% w/w of amorphous canagliflozin, 30-50% w/w of lactose and microcrystalline cellulose, 10-20% w/w of croscarmellose sodium, 1-3% w/w of polysorbate 80 and 0.5-2% w/w of magnesium stearate.

3. The pharmaceutical composition according to claim 1, wherein the granulating fluids are solution of polysorbate 80 in water and lactose in water.

4. The pharmaceutical composition according to claim 1, wherein the composition is coated with coating agent.

* * * * *